US00PP13936P29

(12) United States Plant Patent
Hofmann

(10) Patent No.: US PP13,936 P2
(45) Date of Patent: Jul. 8, 2003

(54) VARIETY OF GERANIUM PLANT NAMED 'PACSAM'

(75) Inventor: Christa Hofmann, Grossdittmannsdorf (DE)

(73) Assignee: Elsner Pac Jungflanzen (DE)

( * ) Notice: Subject to any disclaimer, the term of this patent is extended or adjusted under 35 U.S.C. 154(b) by 12 days.

(21) Appl. No.: 10/118,196

(22) Filed: Apr. 8, 2002

(51) Int. Cl.[7] ..... A01H 5/00
(52) U.S. Cl. ..... Plt./330
(58) Field of Search ..... Plt./330

*Primary Examiner*—Kent Bell
(74) *Attorney, Agent, or Firm*—Webb Ziesenhiem Logsdon Orkin & Hanson, P.C.

(57) ABSTRACT

A new and distinct zonal geranium plant characterized by dark foliage and bright red flowers with oval petals.

1 Drawing Sheet

VARIETAL DENOMINATION

'Pacsam'.

CLASSIFICATION

*Pelargonium×hortorum* (zonal geranium).

BACKGROUND OF THE INVENTION

The present invention comprises a new and distinct cultivar of zonal geranium known by the varietal name 'Pacsam'. The new variety was discovered in Dresden, Germany as the result of in vitro mutation breeding of the unpatented variety 'PAC Somelia'. The new variety exhibits the dark foliage and branching of its parent, but differs in its growth vigor, flower color and flower size. The new variety was first asexually reproduced by cuttings in Dresden, Germany in 2000. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions via cuttings carried out in Dresden, Germany. Plants described were about 9 months old. The color readings were taken indoors on plants grown in pots in greenhouses during Summer. Color references are primarily to The R.H.S. Colour Chart of The Royal Horticultural Society of London.

PLANT

Form: Upright.
Height from media surface to top of foliage: 24–27 cm.
Height from media surface to top of umbels: 30–33 cm.
Growth: Erect, well branched.
Strength: Does not require artificial support.
Roots: Adventive, 155D, 3.5 weeks to develop.

Time to produce a flowering plant: 3 months.
Leaves: Opposite arrangement; zone present.
- *Length.*—3.5–4.0 cm.
- *Width.*—6.0 cm.
- *Shape.*—Overall: Reniform. Base: Cordate. Apex: Pointed.
- *Margin.*—Crenate.
- *Texture.*—Hairy.
- *Color.*—Upper surface: 137A with zone of 139A. Lower surface: 137C.

Ribs and veins:
- *Venation.*—Net-veined.
- *Color.*—137D.

Petioles:
- *Color.*—137D.
- *Length.*—4 cm.

Stem/branches:
- *Color.*—137D.
- *Overall stem length.*—27 cm.
- *Internode length.*—1.5–3.5 cm.
- *Lateral branch length.*—20 cm.

THE BUD

When just beginning to open:
Shape:
- *Overall.*—Umbel-shaped.
- *Individual bud.*—Shell-shaped.

Color: 46B.
Size:
- *Cluster.*—4.5 cm.
- *Individual bud.*—Length: 1.2 cm. Width: 0.8 cm.

INFLORESCENCE

Flowering: Continuous through summer until frost.
Borne: Umbel; flower on pedicel, pedicel on peduncle.
Umbel:
- *Width.*—12 cm.
- *Depth.*—6 cm.
- *Number of flowers per umbel.*—20–25.
- *Lastingness.*—4–6 weeks.

Flowers.
- *Form.*—Zygomorph, semi-double.
- *Size.*—Diameter: 5.0 cm. Depth: 1.5 cm.
- *Petals.*—Color: Upper surface: 46B. Lower surface: 46C. Quantity: 8–10 per flower, including petaloids.

Size: Length: 3 cm. Width: 2 cm. Shape: Overall: Oval. Apex: Round. Base: Pointed. Margin: Entire. Texture: Velvety.

Petaloids:

*Quantity.*—3–4.

*Shape.*—Irregular.

*Color.*—46B (both surfaces).

Sepals:

*Shape.*—Overall: Narrow, linear. Apex: Pointed. Base: Fused.

*Color.*—Upper Surface: 137C. Lower Surface: 137D.

*Size.*—Length: 0.9 cm. Width: 0.3 cm.

Pedicel:

*Length.*—3 cm.

*Color.*—138A with some 178B.

Peduncle:

*Length.*—10–12 cm.

*Color.*—138A with some 179B.

Disease/pest resistance: No susceptibility to diseases or pests noted to date.

REPRODUCTIVE ORGANS

Stamens:

*Anthers.*—2 mm long.

*Filaments.*—*Length:* 8–9 mm. Color: 112D.

*Pollen.*—28A.

Pistils:

*Number.*—One, four to five parted.

*Length.*—3–4 mm.

*Stigma.*—61A.

*Style.*—Length: 0.5 cm. Color: 61A.

Ovaries: Superior, hairy.

*Length.*—0.4–0.6 cm.

*Color.*—138B.

Fruit: If present, maximum five per flower, 0.3–0.5 cm long, 165A.

GENERAL CHARACTERISTICS

1. Compact growth.
2. Intense red colored, velvety flowers.
3. Heat tolerant.
4. Elegant flower shape.
5. Suitability for transportation.
6. Long-lasting flowers.
7. Stable flower color.

I claim:

1. A new and distinct variety of geranium plant substantially as shown and described.

* * * * *

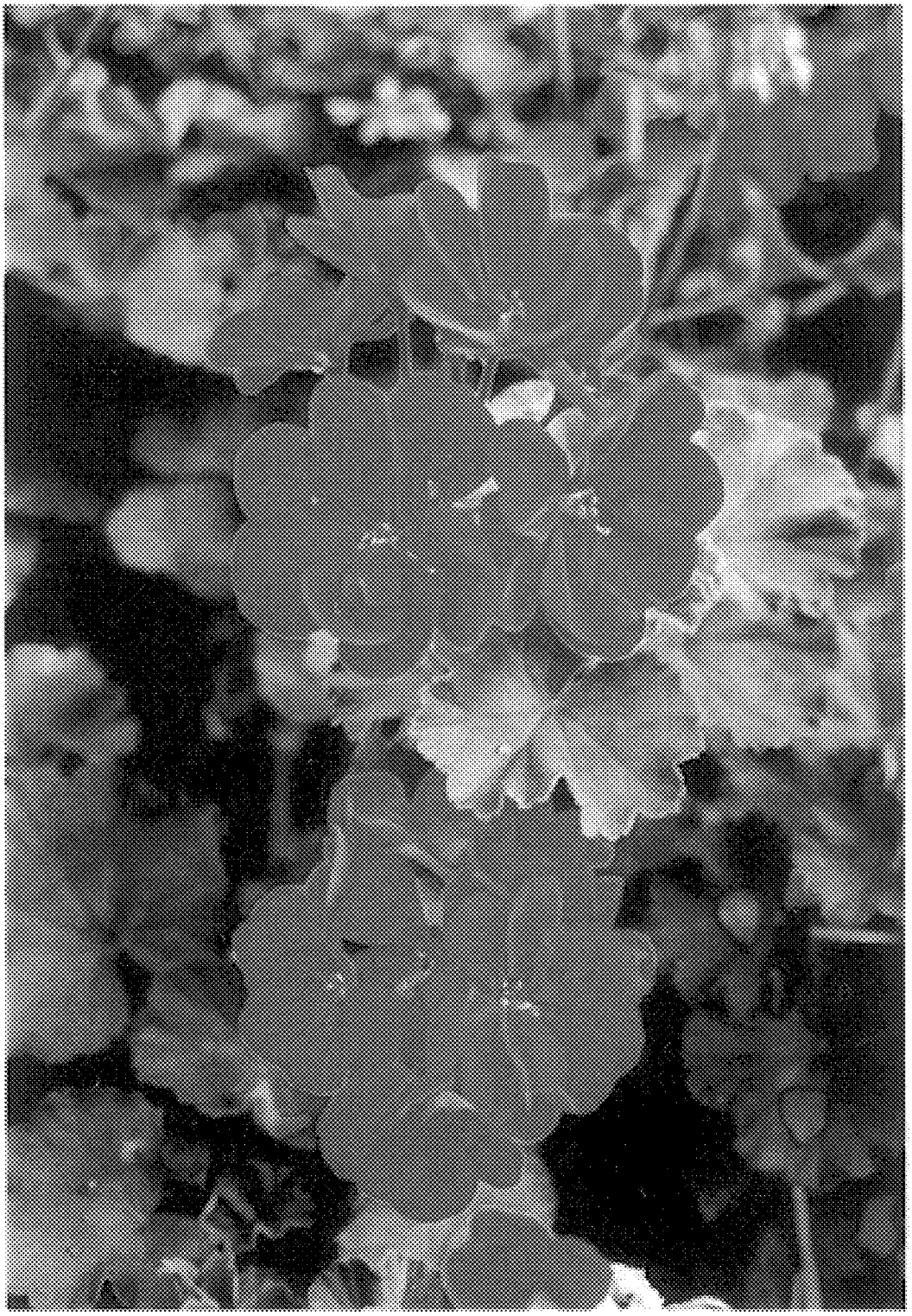

UNITED STATES PATENT AND TRADEMARK OFFICE

CERTIFICATE OF CORRECTION

PATENT NO. : PP 13,936 P2
DATED : July 8, 2003
INVENTOR(S) : Christa Hofmann

It is certified that error appears in the above-identified patent and that said Letters Patent is hereby corrected as shown below:

Title page,
Item [73], Assignee, "Jungflanzen" should read -- Jungpflanzen --.

Column 1,
Line 13, "in vitro" should read -- *in vitro* --.

Signed and Sealed this

Twenty-seventh Day of January, 2004

JON W. DUDAS
*Acting Director of the United States Patent and Trademark Office*